United States Patent

Hageman et al.

(12) United States Patent
(10) Patent No.: US 6,900,180 B1
(45) Date of Patent: May 31, 2005

(54) PHARMACEUTICAL COMPOSITIONS FOR ALLEVIATING DISCOMFORT

(75) Inventors: Robert Johan Joseph Hageman, Waddinxveen (NL); Jacob Geert Bindels, Zoetermeer (NL)

(73) Assignee: N.V. Nutricia, Zoetermeer (NL)

( * ) Notice: Subject to any disclaimer, the term of this patent is extended or adjusted under 35 U.S.C. 154(b) by 0 days.

(21) Appl. No.: 09/889,793

(22) PCT Filed: Jan. 20, 2000

(86) PCT No.: PCT/NL00/00042

§ 371 (c)(1),
(2), (4) Date: Oct. 24, 2001

(87) PCT Pub. No.: WO00/43013

PCT Pub. Date: Jul. 27, 2000

(30) Foreign Application Priority Data

Jan. 20, 1999 (EP) .............................. 99200166
Apr. 29, 1999 (EP) .............................. 99201359

(51) Int. Cl.⁷ ...................... A61K 31/70; A61K 31/50; A61K 31/195

(52) U.S. Cl. ...................... 514/23; 514/21; 514/52; 514/54; 514/249; 514/561; 514/565; 514/159; 514/348; 424/439; 424/682; 426/72; 435/193; 536/23.2; 536/23.5

(58) Field of Search ................. 514/23, 52, 54, 514/249, 561, 565, 21, 159, 348; 424/439, 682; 426/72; 435/193; 536/23.2, 23.5

(56) References Cited

U.S. PATENT DOCUMENTS

| | | | | |
|---|---|---|---|---|
| 5,292,538 A | * | 3/1994 | Paul et al. | 426/74 |
| 5,545,670 A | | 8/1996 | Bissbort et al. | |
| 5,631,271 A | * | 5/1997 | Serfontein | 514/345 |
| 5,792,754 A | * | 8/1998 | Green et al. | 514/60 |
| 6,420,342 B1 | * | 7/2002 | Hageman et al. | 514/23 |
| 6,475,539 B1 | * | 11/2002 | DeWille et al. | 426/72 |
| 6,613,367 B1 | * | 9/2003 | Wells et al. | 426/72 |
| 2002/0147153 A1 | * | 10/2002 | Bell et al. | 514/21 |

FOREIGN PATENT DOCUMENTS

| | | |
|---|---|---|
| DE | 43 26 675 | 2/1995 |
| EP | 0 721 742 | 7/1996 |

* cited by examiner

*Primary Examiner*—James O. Wilson
*Assistant Examiner*—Devesh Khare
(74) *Attorney, Agent, or Firm*—Young & Thompson

(57) ABSTRACT

The invention relates to products for complete nutrition of infants or diseased or elderly persons. The products are characterized by increased levels of folic acid, vitamin B6 and vitamin B12 or their functional equivalents. These products improve feelings of well-being of infants, especially those of young age, and are useful in the treatment and prevention of diseases that are associated with disorders of serotonin and melatonin metabolism.

10 Claims, No Drawings

PHARMACEUTICAL COMPOSITIONS FOR ALLEVIATING DISCOMFORT

FIELD OF THE INVENTION

The invention is related to pharmaceutical and/or nutritional compositions, including infant formulae, for improving feelings of well-being, compensation of immaturity and problems in the metabolic capacity. The nutritional products provide complete nutrition to infants, diseased and elderly people, and their composition is characterised by increased amounts of cofactors. The nutritional products can also be in the form of supplements that provide the cofactors and only a part of the further desirable food components.

BACKGROUND OF THE INVENTION

At present a large part of the population of babies in industrialised countries are fed with specialised infant formulae. It has been reported that consumption of these formulae is associated with several medical problems, such as increased frequency of gastrointestinal problems and decreased immune status. Such problems may occur at young age, but perhaps also at later age, because infants that are exclusively fed with human breast milk would score better on these parameters. It has also been reported that infants that are exclusively fed with these artificial formulae suffer from longer episodes of crying compared to those that are fed with human breast milk. This suggests a general feeling of discomfort due to perhaps hunger, pain or even medical problems. These problems may delay development of the child and produce concerns and practical problems to the parents.

In a first aspect of the invention it is aimed to develop a new infant formula for complete nutrition that decreases the number of crying episodes and promotes sleeping behaviour for the child, especially for infants of young gestational age.

In a second aspect it is also aimed to develop infant formulae that compensate for the relatively small capacity of the (rapidly developing) metabolic systems of the child shortly after birth. This leads to improved health, formation of higher quality new tissue (visual acuity, intellectual capacities, etc.), a better immune status and a decrease in occurrence of periods of increased bilirubin plasma levels (hyperbilirubinaemia or jaundice). Increased bilirubin levels are known to occur relatively often within the first 3 weeks after birth. Some of the negative effects of this disorder have been described in the prior art, including the inhibition by bilirubin of the uptake of the neurotransmitters dopamine and glutamate by the synaptic vesicles and the neurotoxic effects that this disease state may have.

Conventional infant formulae have been developed that mimic the composition of human breast milk to a degree that can be achieved at a reasonable price. These formulae are normally based on cow's milk proteins like casein or mixtures of casein and whey. In case of problems, such as metabolic disorders or allergic reactions, other protein sources are used like hydrolysates or soybean proteins; alternatively the allergic component is replaced by another non-allergenic ingredient. However, the composition of these formulae still differs from that of human breast milk. The relatively low levels of tryptophan and cysteine/cystine can be compensated for by increasing the amount of protein in the product. However, this increases the amount of threonine to very high levels and increases the costs of the formulae. Also the imbalances with regard to the ratio of tryptophan to the sum of the large neutral amino acids will be maintained.

In a further aspect, the invention is related to the use of folic acid, vitamins B12 and B6 or their functional analogues in the manufacture of compositions for the prevention and/or treatment of specific neurological disorders. The invention also covers the products that are obtained by such use. Products according to the invention will be effective in improving sleep behaviour, insomnia, mood, decrease feelings of fear and depression and increase feelings of well-being. In addition, undesirable symptoms related to neuro-degenerative disorders like Alzheimer, Parkinson and schizophrenia are decreased. Also, the products can be helpful in the prevention and/or treatment of symptoms associated with restless legs syndrome, myoclonus (a disorder that is often accompanied by muscle contractions and seizures), Gilles de la Tourette, phenylketonuria, multiple sclerosis, analgesia, epilepsy, mania, aggressive behaviour, bulimia and other disorders associated with saturation feelings after eating, ADHD, and psychiatric disorders associated with ageing. Large parts of the population suffer from one of these disorders. Application of common drug therapy may result in undesired side effects, such as addiction and ineffectivity, and may lead to functional deficiencies of food components. So there is a need for a pharmaceutical or nutritional formulation that helps prevent or treat these disorders and does not result in these side effects.

Sandyk, R., reported in *Intern. J Neuroscience*, 1992, 67, 127–144 that several, but not all, of these disorders were associated with decreased serotonin levels in the brain and reviewed some of the relevant literature about the use of tryptophan to restore serotonin levels in the brain.

We believe, however, that all these disorders are associated not only with a disorder in serotonin levels, but also with the melatonin levels in the brain, the presence of pterines and folate in the brain and the functioning of the methylating system in the body. The latter may become evident by abnormal systemic adenosine levels. Because relatively very little serotonin or melatonin is present in the normal diet, most endogenous amounts must originate from biosynthesis. An increase in the brain levels of both serotonin and melatonin can therefore only be achieved by increasing the metabolic capacity of the serotoninergic neurons. An increase of the brain levels of both serotonin and melatonin and the presence of reduced folic acid and pterins in the brain would lead to a relief of the clinical problems.

Sandyk disclosed that in some cases administration of an effective amount of the natural precursor of serotonin, tryptophan, could lead to increased levels of serotonin in brain tissue. This idea was also subject of a number of other publications, which appeared in the past.

WO 87/01590 (=EP-A-238533, Kreitzman) discloses a slimming diet for adults that provides per day less than 1000 kcal (so less than 14 kcal/kgbw.d; less than 700 kcal/day is preferred), less than 100 g protein (which results in less than 1.4 g protein per kgbw per day for a 70 kg person; always more than 30 g and less than 46 g protein is preferred) and more than 0.5 g tryptophan (more than 3 g is preferred). The product is unsuitable for feeding infants due to too high protein levels and potential toxicity of the amount of tryptophan that is included. The product should also not be used for combating obesity of the infant.

EP-A-007691 (Wurtman) discloses a formula for suppression of appetite for carbohydrates in adults, which comprises tryptophan, in an amount of 10–100 mg per kgbw.d, and carbohydrates, but no branched-chain amino acids. The ratio of the amounts of tryptophan and carbohydrates in the formula must be 1: 3–50. The product is unsuitable for use in infants, because infants require branched chain amino acids at young age for growth.

WO 91/10441 (=EP-A-463154) discloses compositions comprising polypeptides containing more than 2.2% tryptophan as well as arginine or ornithine for providing a "serotinergic effect". The product is developed for combating obesity in adults and treating feelings of depression. Preferably α-lactalbumin is used as a source of tryptophan, which possesses a high ratio of tryptophan to large neutral amino acids plus methionine. Vegetable proteins are suggested as attractive ingredients, because of their relatively high amount of arginine and relatively low levels of phenylalanine and tyrosine. The latter two amino acids are however essential amino acids and recommended daily intakes should be ensured.

WO 98/14204 discloses the use of α-lactalbumin as nutritional complement or medicine for regulating sleep, especially when a jet lag is observed. Consumption of 100 mg and 250 mg α-lactalbumin is claimed to be effective in adults. No relation is made to use in infants nor is indicated that vitamins might play a role in regulating sleep. Alpha-lactalbumin was shown to have a value of the ratio of tryptophan to the sum of the large neutral amino acids is about 0.074 and that of the ratio Cys to Trp equals about 1.47, while the amount of tryptophan is relatively high (about 3.0%).

Heine discloses the use of hydrolysed α-lactalbumin as protein source in infant formulae in DE-A-4130284. Use of this protein hydrolysate was claimed in order to achieve a clear separation with β-lactoglobulin and thus administer a better-balanced composition with regard to threonine, tryptophan and cysteine/cystine. No reference was made to specific positive effects that can be obtained by using intact α-lactalbumin with regard to feelings of well-being nor the support of insufficiently functioning metabolic systems by using the products of the invention. No indication is given that folic acid, vitamin B12 and B6 play a crucial role in these respects. The products disclosed by Heine are also more expensive and have a worse taste compared to the products of the present invention.

After consumption of carbohydrates, insulin is released from the pancreas. This latter component is known to reverse the catabolic processes in the body, that may have resulted from a period of starvation prior to the (re)feeding of the child, into anabolic processes. As long as sufficient glucose is present in the plasma, plasma insulin levels remain sufficiently high to prevent catabolism of (in particular muscle) tissue and the resulting release of branched chain amino acids (BCAA, valine, isoleucine and leucine). In a further aspect, the invention is therefore aimed at developing formulae that provide an insulin response on a short term, with a sufficient longer-term effect as well.

Infants, especially those of young gestational age, are extremely sensitive to consumption of excess amounts of food components and imbalances in the consumption pattern of these components, predominantly due to their low relatively metabolic and clearance capacity. This is caused by inherited problems and immaturity of their enzymatic systems and the small capacity of their organs. Infants are also sensitive to imbalances in neurotransmitter levels in the brain. It is therefore dangerous to transfer concepts that are developed for healthy adults to infant formulae. The composition of human breast milk is therefore mostly taken as "golden standard". In another aspect of the invention, a nutritional product is aimed at that does not cause any toxic reactions in normal use and to deviate as little from the golden standard as is justified.

It is important to recognise that all the aspects as mentioned above must be achieved at the same time, in order to improve well-being satisfactorily without causing negative effects to the child. Also elderly people may suffer form an imparted metabolic capacity and especially the group having neurodegenerative disorders should not be exposed to inbalanced food.

According to the prior art, relatively high doses of tryptophan have to be administered, optionally in the relative absence of large neutral amino acids and accompanied with digestible carbohydrates, in order to see clinical benefits. This approach leads to several problems. In some patients no or very little effect is observed. Administering high doses of tryptophan may lead to undesired side-effects, especially in those patients that have a low metabolic capacity or are deficient in certain vitamins or minerals. Examples of these patients are persons that are at risk for or are suffering from diabetes mellitus or bladder cancer, persons that are subjected to drug therapy, persons suffering of renal problems, young infants and elderly persons. Also, it appeared to be very difficult to estimate for a particular person the exact requirement of tryptophan for obtaining optimal serotonin levels and it is unknown how high these desirable serotonin levels are.

It has now been found that the restoration of the patient's capacity to metabolise tryptophan to serotonin and especially melatonin, is an approach that does not demonstrate the above-mentioned disadvantages. It allows the natural mechanisms to regulate endogenous levels, without subjecting the organism to high levels of potentially toxic tryptophan.

This can be achieved by administering extra amounts of certain cofactors, at least folic acid, vitamin B12 and vitamin B6. In this situation it is often not required to supplete tryptophan; however, in those cases that persons are deficient in tryptophan, administration of relatively little amounts of tryptophan already gives significant improvement of the clinical symptoms.

In cases where a patient has a limited capacity for serotonin biosynthesis, e.g. by damage to tissue that is rich in serotoninergic neurons or due to an inherited disorder, administration of cofactors appeared to increase serotonin and melatonin levels in the brain, if a certain basal level of tryptophan was available.

It was found that the cofactors of interest are at least folic acid, pyridoxal phosphate and vitamin B12 or their functional equivalents. In addition it may be required to administer riboflavin, thiamine and niacin, or their functional equivalents.

The biochemical roles of folic acid, vitamin B6 and B12 are described in the art. To the best of the knowledge of the inventors, it is nowhere described or indicated that consumption of the combination of these vitamins, in amounts as given in the claims, is crucial for increasing well-being and normalising behaviour, senses of pain, and mood of the infant, and elder persons. It was found that the restrictions in protein and carbohydrates composition, that are present for infant formulae, necessitate the increase in these vitamins in order to have an optimal effect. It is also not earlier disclosed that inclusion of these vitamins in the amounts as claimed, significantly enlarges the group of infants that benefit from such infant formulae, especially with regard to increase of well-being, the improvement of other serotonin or melatonin-mediated disorders.

Also, the amounts of all three essential vitamins, being folic acid, vitamin B6 and B12 are insufficient to support biosynthesis and metabolism, including the serotonin metabolism, in the young child.

DETAILED DESCRIPTION OF THE INVENTION

The characteristics of the composition according to the invention are described in the claims and in more detail below. For optimal effectivity at least 200 μg folic acid, at least 1.9 μg vitamin B12 and at least 0.3 mg vitamin B6 is required per daily dosage, and preferably at least 300 μg, at least 4.8 μg and at least 3.0 mg of respectively folic acid, vitamin B12 and vitamin B6.

In most cases also at least 0.5 mg riboflavin (vitamin B2), 1.0 mg thiamine (vitamin B1) and at least 2 mg niacin per daily dosis is required. Deficiencies on the latter components occur relatively often in the above-mentioned groups of patients and these will lead to imparted generation of ATP and reducing power in the form of NAD(P)H. Riboflavin is also required for activating pyridoxal. Low ATP levels are deleterious to the metabolic capacity to methylate and the biosynthetic capacity for melatonin and serotonin.

It is further highly desirable that digestible carbohydrates that can serve as glucose source are included in the product. Examples are glucose polymers, lactose and sucrose. This ensures a continuous supply of reducing equivalents in the form of NADH and improves in some instances the transport of tryptophan from blood into the brain. A product according to the invention should advantageously comprise at least 5 g digestible carbohydrates and preferably more than 10 g on a daily basis. Per 100 kcal (419 kJ) of product, the amount of digestible carbohydrate is in the range of 4–25 g, preferably 6–22 g.

The product should further preferably comprise magnesium to improve methylation, and zinc to improve total metabolism of sulfur amino acids. Magnesium also stabilises the NMDA receptor. An overstimulation of the NMDA receptor is associated with many of the above-mentioned disorders and maintenance of an overstimulation of this receptor is claimed to aggravate some of the symptoms that are observed in some of these diseases. Zinc is further involved in the modulation of neurotransmitter receptors. Zinc should best be above 0.7 mg/100 kcal, which results in a daily intake of at least 3.6 mg. Magnesium should best be included in an amount of at least 5 mg/100 kcal, leading to a daily consumption of at least 36 mg. On the other hand, the amounts of calcium and phophorus should not be too high. Specifically, the weight ratio of Mg+Zn to Ca should be more than 0.08, preferably more than 0.10, and the weight ratio of Mg+Zn to P should be more than 0.2, preferably more than 0.26 (and Ca+Mg+Zn/P>1.9).

Tryptophan can be included in an amount of 0.05–3 g per daily dose, in particular 0.3–1.2 g. Preferably tryptophan is supplied in the form of a protein. The protein must have an amino acid composition that is characterised by a high ratio of tryptophan/large neutral amino acids, preferably in the range of 0.048–0.2. Alfa-lactalbumin was found to be a suitable protein.

It is also advantageous to include melatonin in the product, especially in those products that are meant to be used in the evening. Melatonin upregulates certain enzymes that play an important role in the detoxification of radicals that are created in the highly firing neurons and that may play a role in the pathogenesis of the disorders mentioned above. Melatonin also can help to set and regulate the circadian rhythm, which can be very helpful in the treatment of sleeping disorders and depression. Melatonin can be included in an amount of 0.5–5 g per daily dosage.

Also adenosine can be used to set the circadian cycle; an amount of 50–1000 g per daily serving is recommended.

Betaine, choline, methionine or their functional equivalents should be included in those situations that is suspected that the patient suffers from a lack of food components that provide methyl groups. Examples are the elderly or schizophrenic patients that often have very poor eating behaviour. Betaine is the preferred source because it also can serve as a precursor for choline that is useful for synthesis or myelin or repair of damaged neurons and because it has an excellent taste. Obviously also choline itself can be used. Betaine can be included in an amount of 30–4000 mg and preferably 50–600 mg per daily dosage.

Methionine can be included in an amount of 50–1000 mg and preferably 100–500 mg per daily dosage. Vitamin K (phylloquinones, menaquinones and other naphthoquinones) or its functional equivalent is preferably included at a level of at least 8 μg, preferably at least 30 μg per 100 kcal. For elderly persons, a daily minimum of 1 mg is found to be beneficial.

Other minerals, trace elements and vitamins can be included in amounts that comply with the recommendations as set by the National Research Council (US) or other official institutes.

The preferred amounts of all components depend on the group of patients for which the product is developed. Young infants would normally require lower amounts than adults; elderly suffering from a severe form of Alzheimer would normally benefit from less of the active components than a young adult that is suffering from the syndrome of Gilles de la Tourette.

Typical amounts per 100 kcal of the product are summarised in Table 1.

TABLE 1

| Component | Amounts per 100 kcal product | | |
|---|---|---|---|
| | Range | Preferred range | |
| Digestible carbohydrates | 4–25 | 6–22 | g |
| Folic acid | 44–4000 | 50–2000 | μg |
| Vitamin B12 | 0.8–2000 | 1–1000* | μg |
| Vitamin B6 | 50–10000 | 60–2000 | μg |
| Riboflavin | 0.08–20 | 0.14–6 | mg |
| Thiamine | 55–8000 | 70–4000 | μg |
| Niacin | 0.55–60 | 1.4–25 | mg niacin equivalents |
| Vitamin K | >8 | 30–90 | μg |
| Taurine | 5–100 | 7–50 | mg |
| Betaine | 50–4000 | 30–600 | mg |
| Magnesium | 5–400 | 8–200 | mg |
| Zinc | 0.8–100 | 1–30 | mg |
| Mg + Zn/Ca | >0.08 | >0.10 | m/m |
| Mg + Zn/P | >0.20 | >0.26 | m/m |
| Melatonin | 30–3000 | 60–800 | mg |
| Tryptophan | 0.05–8 | 0.2–2* | g |
| Adenosine | 1–1000 | 50–500 | mg |
| Methionine | 50–1000 | 100–500 | mg |

Note *higher doses should preferably be given as a multifold of smaller doses.

Infant Formulae

Energy density: The energy density of the product is similar to that of prior art products and is in the range of 62–73 kcal/100 ml liquid or reconstituted product. Preferably the energy density is in the range of 64–71 kcal/ml.

Proteins: Protein levels in a product can be determined with the classical Kjeldahl method. The result reflects the crude proteins that are present. For the purpose of this invention we define the protein level as the amount of real proteins plus the amount of amino acids, their salts and peptides; so non-protein nitrogen is excluded. In the products of the invention the protein levels will be in the range of 1.0–3.0 g per 100 kcal, especially between 1.0 and 2.4 g/100 kcal, which allows complete satisfaction of the infants protein needs. An amount of 1.5–2.2 g/100 kcal is most preferred. The higher protein levels, such as from 2.0 or from 2.4 to 3.0 are especially suitable in combination with increased levels of folic acid, vitamin B6 and/or vitamin B12. Conventional proteins like those from cow's milk or soybeans can be used as basic protein sources, as they provide sufficient amounts of all essential amino acids but also branched-chain amino acids.

In order to increase the amount of L-tryptophan in the product, free L-tryptophan, or a functional equivalent thereof like tryptophan salts or tryptophan-rich peptides, can be suppleted. If free L-tryptophan is used, special care is taken to remove all impurities that might cause toxic reactions. It is further preferred to use a tryptophan source that is stable under the conditions that the infant formula is manufactured. A suitable source is a tryptophan-rich protein or a hydrolysate or extract thereof. If proteins are used as ingredient, it is obvious that the levels of the large neutral amino acids (Tyr, Phe, Val, Leu, Ile) and threonine are relatively low. However they should not be that low, that the recommended daily intakes are not met. Examples of suitable proteins in this respect are acid whey, α-lactalbumin, egg protein and proteins from meat and wheat, and mixtures of two or more of these components. Acid whey protein or unhydrolysed α-lactalbumin are especially preferred, because of the excellent amino acid profile and the sustained release pattern in young children compared to hydrolysates thereof or compared to a combination of mixtures of alternative dairy products and suppleted sources of tryptophan, cysteine or arginine. Tryptophan should be present in the product in an amount of 1.6–3.5 g, especially 1.7–3.5 g per 100 g of the total protein component and preferably in an amount of 1.9–2.8 g/100 g protein.

The value of the ratio of the amounts in the product of tryptophan and the sum of the large neutral amino acids must be in the range 4.8–10 and preferably in the range 5.5–8.5/100, and most preferably 6.2–8.2/100. When threonine is also considered as a large neutral amino acid, the value of the ratio must be in the range 4.1–8.0 and preferably in the range 4.7–7.5.

In order to ensure sufficiently high levels of cysteine, whey proteins or egg proteins can be included in the formula. If whey proteins are used, acid whey is recommended, in order to avoid too high threonine levels. It is especially preferred to have a relatively high ratio of Cys/Trp in the range of 0.8–1.4, in order to support optimally inclusion of cysteine in liver proteins and in glutathione, which is required for optimal growth and immune function.

In order to increase insulin response arginine or lysine can be supplied as L-forms of the free amino acid or as their functional equivalents. Functional equivalents of amino acids can for example be their salts, synthetic peptides, or proteins that are rich in the particular amino acid, or extracts or hydrolysates of these proteins. Also mixtures of proteins can be included. For example mixtures of 40% casein and 60% whey could be suppleted with the hydrochloric salts of L-tryptophan or L-arginine. It is however preferred to include arginine in a form that is slowly released such as by using a granulate or similar system that comprises an arginine salt like L-arginine.HCl, or by using partially pea protein, or a hydrolysate or extract thereof, in order to extend the insulin effect. The total amount of arginine plus lysine should exceed 200, preferably exceed 250 mg/kg, e.g. 280 mg/kgbw.d. The amount of protein that is required for providing this amount of arginine can be calculated from this number and the concentration of arginine or lysine in this protein.

Carbohydrates: According to the invention, the amount of carbohydrates in the formula must be in the range of 9–15 g/100 kcal (35–60 en %), and preferably in the range of 11–14 g/100 kcal. This results in a carbohydrate content of 5.7–10.5 g per 100 ml of liquid or reconstituted product. The ratio of the amount of carbohydrates to the amount of tryptophan will exceed 20 and preferably 50, and go up to 940, preferably up to 450. The weight ratio of carbohydrates to protein is preferably from 5 to 14, most preferably from 6 to 12.

It is preferred to use, at least partly, maltodextrins, apart from the lactose that may be present in the formula. This will ensure a fast availability of glucose units in plasma and therefore a fast insulin response. However, it is preferred to include at least 50% of the carbohydrates as lactose, except in those cases that the product will be used by lactose-intolerant infants. If maltodextrins are used it is advantageous to use maltodextrins having a degree of hydrolysis of 10–15 dextrin equivalents, in order to decrease the sweetness of the product.

Folic acid: Folic acid can occur in nature in many forms. Typically it is suppleted to infant formulae as monoglutamate. Though according to the invention basically all functional equivalents of folic acid can be used, it is preferred to use the monoglutamate form for obtaining best bioavailability. It is essential to include at least 44 µg per 100 kcal. If higher amounts of folic acid are consumed, a larger group of infants will show an improved serotonin- and melatonin metabolism, even if the amounts of tryptophan are relatively low as in conventional infant formulae. This is especially true if the amount of folic acid is above 50 µg per 100 kcal and sufficient vitamin B12 is made available, as is the case when the formula is suppleted with more than 0.6 µg/100 kcal, as is indicated below.

Vitamin B12: Vitamin B12 is normally present in infant formula partially as a complex with dairy proteins and predominantly as suppleted cyanocobalamine. Before it is absorbed the complex has to be split in the stomach and the released cyanocobalamine has to bind to a factor that is released from the stomach. Once absorbed, cyanocobalamine or alternative forms have to be converted to methylcobalamine, before they can be used as a cofactor that catalyses the conversion of homocysteine to methionine. Both absorption and conversion of cyanocobalamine occur ineffectively in part of the population of young infants.

According to the invention it is therefore required to supplete at least 0.1 µg, and preferably more than 0.8 µg vitamin B12 per 100 kcal, preferably as hydroxycobalamine or a stabilised form, in order to support serotonin biosynthesis and metabolism effectively. Instead of vitamin B12, metabolic equivalents, i.e. compounds that lead to endogenous formation of vitamin B12, can also be used.

When indigestible carbohydrates are added to the product or other bifidogenic measures are taken, these are selected in such a way that the biosynthesis capacity of the gut flora is not imparted or even is stimulated.

Vitamin B6: Vitamin B6 is active in the cells as pyridoxal phosphate. However pyridoxine or pyridoxamine are frequently used as source of this vitamin, because of the stability of these compounds. Infants, especially those of young age, have a restricted capacity to convert these compounds to the active form. It has been found that a simple increase in the dose may decrease the intracellular pyridoxal phosphate levels. It is therefore preferred to include in the formula 50–130 µg vitamin B6 per 100 kcal. If higher amounts of vitamin B6 are suppleted, it is not recommended to use pyridoxine. Also mixtures of pyridoxamine or pyridoxal can be used.

Zinc: It is desirable that the amount of zinc is in the range of 0.7–2 mg/100 kcal, preferably from 0.7 to 1.0 mg/100 kcal. Zinc can be included as a zinc salt, such as zinc chloride or as a complex with amino acids or other components.

Niacin equivalents: Niacin functions in the human body as precursor of NAD and can be synthesised from tryptophan in the adult liver. This predominantly occurs when excess tryptophan is present. Thus tryptophan can also be used as a niacin equivalent (60 mg Trp=1 niacin equivalent). Biosynthesis of niacin is supported in the young child by the characteristic features of the composition as claimed. This permits the availability of sufficient niacin to support the metabolic processes in the child. These can be further supported by increase of the included amount of niacin to a level of 1.2–5 mg/100 kcal.

Apart from the essential components as indicated above, other microingredients may advantageously be included in a complete infant formula, according to EEC 91/321 or corresponding Regulation: these include: Betaine, choline; taurine, inositol, calcium, phosphorus, magnesium, iron, manganese, copper, iodine, sodium, potassium, chloride, selenium, fluoride, carnitine, nucleotides, cholesterol, vitamin A, vit. D, vit. E, vit K, thiamine, riboflavin, pantothenic acid, biotin, and ascorbic acid.

Fats are included in the range of 40–57 en %. The composition of the fat can be selected from prior art compositions. Specially preferred are the ones that are disclosed in any of the earlier patents of patentee, e.g. EP-A404058, EP-A-231904, EP-A-784437 and DE 19644518, which are incorporated by reference. The essential fatty acids that are present must preferably have the cis-configuration. Alpha-linolenic acid (=ALA): 1.75–4.0% and linoleic acid (LA): 8–35% of total fatty acids; the ratio LA/ALA=5–16.

The product of the invention can have the form of liquid or a powder, that can be reconstituted with water to produce a ready to feed formulation. It can also have the form of a meal that is used for weaning purposes or similar product evident to a person skilled in the art. The liquid products can be packaged in bottles, cartons and the like. The powdered products can be packaged in vacuumised packs, cans or sachets and other suitable forms that are known to a person skilled in the art.

It has been found that daily consumption of the infant formulae as described above results in the benefits as described below:
- improves feelings of well being by the infants,
- supporting regular eating and sleeping patterns
- helps to compensate for insufficient capacity of the metabolic systems, especially in the young infant
- consumption of these formulae results in plasma levels of amino acids that are more similar to those of infants, that are exclusively fed with human breast milk, compared to consumption of conventional formulae
- does not give negative side effects to the infant
- therefore improves health and immune status and supports growth of high quality
- has an excellent taste and can be produced at acceptable costs.

EXAMPLES

Example 1

A liquid infant formula having the composition as presented in table 2 was prepared.

TABLE 2

Composition of liquid infant formula
Values are in mg per 100 ml, except where indicated differently.

| | |
|---|---|
| Protein (60% sweet whey, 40% casein) | 1400 |
| Added Trp | 10 |
| Added Arg | 10 |
| Lactose | 7500 |
| Maltodextrins (10–15 DE) | 1600 |
| Fat (EP-231904) | 3100 |
| Na | 18–25 |
| K | 60–100 |
| Cl | 40–60 |
| Ca | 50–85 |
| P | 20–50 |
| Mg | 4.5–6 |
| Fe | 0.5–0.9 |
| Zn | 0.6–1.3 |
| Cu | 40–60 µg |
| Mn | 5–20 µg |
| Se | 1.5–2.2 µg |
| I | 5–15 µg |
| Vitamin A | 80–90 RE |
| β-Carotene | 0–40 µg |
| Vitamin D | 1–1.6 µg |
| Vitamin E | 0.8–1.4 mg TE |
| Vitamin K | 4–20 µg |
| Thiamine | 35–45 µg |
| Riboflavin | 110–150 µg |
| Niacin | 0.7–1.0 mg NE |
| Pantothenate | 0.25–0.35 |
| Biotin | 1.5–1.7 µg |
| Ascorbic acid | 5–10 |
| Taurine | 4–7 |
| Folic acid (added as monoglutamate) | 25–32 µg |
| Vitamin B12 (added as hydroxycobalamine) | 0.4–0.7 µg |
| Vitamin B6 (added as pyridoxine) | 50–65 µg |

This product can be used for improving sleeping behaviour of young infants.

Example 2

Product to be used for the elderly or toddlers as a bedtime drink:

Powdered supplement packed in a can under nitrogen; 10 g to be reconstituted in fruit juice or milk before going to bed.

To 8 kg maltodextrin DE19 are added:

2.0 kg alfa-lactalbumin 50 mg melatonin 100 mg folic acid monoglutamate 25 mg cyanocobalamin 100 mg pyridoxal 100 mg riboflavin 60 mg thiamine.HCl 30 g zinc chloride.12H20

A proper aliquot is filled in the can, e.g. 400 g.

Example 3

Product to be used for ADHD infants or Alzheimer patients.

Powdered product packed in a 10 g sachet. The sachet is to be mixed with a portion of breakfast cereal and reconstituted in milk.

The powder is obtained by mixing:

9.5 kg Maltodextrin 100 mg folic acid 25 mg vit. B12

100 mg B6

100 mg B2

60 mg B1

1.0 g niacin 100 g betaine 300 g magnesium chloride 30 g zinc chloride 50 g adenosine 100 mg Vitamin K

What is claimed is:

1. A composition, comprising carbohydrates, fats and proteins, and containing more than 44 µg up to 4000 µg of folic acid, more than 0.8 µg up to 2000 µg of vitamin B12 and more than 50 ug up to 10,000 µg of vitamin B6 per 100 kcal of said carbohydrates, fats and proteins, and further containing at least one of riboflavin, thiamine, niacin and zinc.

2. A method for treating serotonin- or melatonin-mediated mood or sleep disorders, comprising administering to a person in need of such treatment a composition for complete nutrition comprising carbohydrates, fats and proteins, the composition further containing an effective amount of a combination of more than 44 µg up to 4000 µg of folic acid, more than 50 µg up to 10,000 µg of vitamin B6 and more than 0.8 µg up to 2000 µg of vitamin B12 per 100 kcal of said carbohydrates, fats and proteins and at least one component selected from the group consisting of riboflavin, thiamine, niacin and zinc.

3. The method according to claim 2, in which the composition is a composition for complete nutrition of infants.

4. The method according to claim 2, in which the composition is a composition for complete nutrition of diseased or elderly persons.

5. The method according to claim 2, in which the composition further contains at least 0.55 mg of niacin and/or at least 0.08 mg of riboflavin and/or at least 55 µg of thiamine per 100 kcal.

6. The method according to claim 2, in which the composition further contains more than 50 mg of choline or betaine or the sum thereof, and/or at least 5 mg of taurine, and/or at least 50 mg of methionine per 100 kcal.

7. The method according to claim 2, in which the composition further contains 0.05–8 g of tryptophan and/or 30–3000 mg of melatonin and/or 50–1000 mg of adenosine per 100 kcal.

8. The method according to claim 2, in which the composition further contains 5–400 mg magnesium and/or 0.7–100 mg zinc per 100 kcal, and calcium, and having a weight ratio of magnesium plus zinc to calcium of higher than 0.08.

9. The method according to claim 2, in which the composition contains 9–15 g of carbohydrates per 100 kcal.

10. The method of claim 2, comprising administering an amount of at least 200 µg of folic acid, at least 2 µg of vitamin B12 and at least 2 mg of vitamin B6 per daily dosage.

* * * * *